(12) United States Patent
Chung

(10) Patent No.: US 8,029,474 B2
(45) Date of Patent: Oct. 4, 2011

(54) TROCAR FOR LAPAROSCOPIC SURGERY

(76) Inventor: Hyun-Kook Chung, Gyeonggi-do (KR)

( * ) Notice: Subject to any disclaimer, the term of this patent is extended or adjusted under 35 U.S.C. 154(b) by 0 days.

(21) Appl. No.: 12/740,867

(22) PCT Filed: Mar. 31, 2009

(86) PCT No.: PCT/KR2009/001635
§ 371 (c)(1),
(2), (4) Date: Apr. 30, 2010

(87) PCT Pub. No.: WO2010/027135
PCT Pub. Date: Mar. 11, 2010

(65) Prior Publication Data
US 2010/0268164 A1 Oct. 21, 2010

(30) Foreign Application Priority Data
Sep. 4, 2008 (KR) ........................ 10-2008-0087450

(51) Int. Cl.
*A61M 5/178* (2006.01)
(52) U.S. Cl. .............................. 604/167.03; 604/164.01
(58) Field of Classification Search ............ 604/164.01, 604/164.02, 164.04, 164.06–164.11, 165.01–165.04, 604/167.01–167.06
See application file for complete search history.

(56) References Cited

U.S. PATENT DOCUMENTS
2008/0171987 A1 7/2008 Franer et al.

FOREIGN PATENT DOCUMENTS
JP 2005-103291 A 4/2005
KR 10-0786728 B1 12/2007

*Primary Examiner* — Nicholas D Lucchesi
*Assistant Examiner* — Nathan R Price
(74) *Attorney, Agent, or Firm* — Hayes Soloway P.C.

(57) ABSTRACT

The present invention relates to a trocar for laparoscopic surgery for performing the laparoscopic surgery through a surgical instrument by making a puncture in the abdomen of a patient, the trocar including: a head unit 10 including an upper case 11 and a lower cover 12; a base unit 20 including a lower case 24 having a trocar sleeve fixing protrusion 21 in a lower part thereof and a coupling member 25 installed at an upper surface thereof; a trocar sleeve 17 installed at the trocar sleeve fixing protrusion 21; a lip valve 60 installed within the head unit 10 and having a tapered lower part; an insertion unit 30 installed at the upper part of the lip valve 60; a button unit 40 including a button 41 elastically installed at an elastic bush 43; and a trocar needle 50 introduced into the trocar sleeve 17 through the lip valve 60 or the insertion unit 30.

2 Claims, 7 Drawing Sheets

TROCAR FOR LAPAROSCOPIC SURGERY

BACKGROUND OF THE INVENTION

1. Field of the Invention

The present invention relates to a trocar for laparoscopic surgery, and more particularly, to a trocar for performing laparoscopic surgery by making a small hole instead of opening the abdomen of a patient for surgery.

Specifically, when making a puncture in the abdomen, internal organs can be protected by installing a sliding rod within a support pipe of a trocar needle that is inserted into a trocar sleeve and makes a puncture in the patient's skin.

Further, since a head unit of the trocar includes a packing to which elastic fibers are attached, a flexible tube, and a sleeve, even though any on of other surgical instruments having smaller diameter than that of the trocar sleeve installed at the abdomen is inserted into the head unit, external air and inner carbon dioxide can be prevented from being injected and discharged through the packing when performing laparoscopic surgery.

Further, the present invention relates to a trocar for laparoscopic surgery for easily taking out gauzes and extracted materials of internal organs generated when performing the surgery.

2. Description of the Related Art

A trocar is generally used when laparoscopic surgery is performed.

In a conventional trocar, after a sleeve pipe that accommodates a trocar needle and that is installed within a head unit is fixed and installed corresponding to a trocar sleeve coupled to the lower end thereof, a separate movable piece corresponding to an end portion of the sleeve pipe is suppressed by elasticity of a spring, thereby maintaining airtightness.

When the trocar needle is inserted into an injection port of the sleeve pipe, a needle rod is inserted into a trocar sleeve while pushing the movable piece corresponding to the end portion of the sleeve pipe, and thus an end portion of the trocar needle is protruded.

The trocar may cause damage to internal organs of the abdomen by a perforating force while making a puncture in the abdomen of a patient, and therefore making a puncture in the abdomen should be carefully performed, and if the internal organs are erroneously damaged, recovery may be delayed due to the damaged internal organs.

Further, in order to perform laparoscopic surgery, a plurality of trocars are inserted into the abdomen of a patient and in this case, a single needle rod is inserted into any one of the plurality of trocars already inserted into the abdomen.

When performing surgery in the abdomen using an endoscope, in order to secure a visual field for surgery, the space therefor is maintained by injecting carbon dioxide through a valve and the movable piece corresponding to the end portion of the sleeve pipe closely contacts by elasticity of a spring interposed at one side of a shaft.

Therefore, when an elastic force of the spring is not uniformly distributed in a close contact surface of the movable piece, carbon dioxide may be leaked.

Further, after surgery has been performed, carbon dioxide is discharged through a separate means instead of being discharged through a head unit of the trocar and thus a discharge time of carbon dioxide may be delayed.

Particularly, because the conventional trocar is an expensive product, the trocar is reused after washing and disinfecting instead of disposing after using and thus an inanitary problem may occur.

When using several kinds of surgical instruments having different diameters, separate head units corresponding to diameters of each of the surgical instruments should be provided and exchanged and thus it may be inconvenient and take long time.

SUMMARY OF THE INVENTION

Technical Problem

The present invention has been made in view of the above problems, and provides a trocar for laparoscopic surgery that can prevent external air from being injected into the abdomen when taking out a surgical instrument from a trocar sleeve or when introducing a surgical instrument into a trocar sleeve in order to perform laparoscopic surgery instead of performing open surgery when performing a surgical operation of internal organs within the abdomen.

The present invention further provides a trocar for laparoscopic surgery that can prevent a trocar sleeve from being removed from the abdomen when performing laparoscopic surgery.

The present invention further provides a trocar for laparoscopic surgery that can prevent external air from being injected into the abdomen and prevent carbon dioxide from being discharged through maintaining airtightness by a packing closely contacting with an outer peripheral surface of a surgical instrument even though any one of surgical instruments of different sizes necessary for performing laparoscopic surgery is used.

The present invention further provides a trocar for laparoscopic surgery that can easily take out gauzes or extracted internal organs when performing laparoscopic surgery by using an extension button in order to open and close the lower end of a lip valve.

Technical Solution

In accordance with an aspect of the present invention, a trocar for laparoscopic surgery for performing the laparoscopic surgery through a surgical instrument by making a puncture in the abdomen of a patient, the trocar includes: a head unit including an upper case having an installation hole in an upper part thereof and having a stopper groove in an inner circumferential surface of the installation hole, and a lower cover installed at the bottom of the upper case and having a stopper piece at a periphery of an upper surface of the lower cover; a base unit including a lower case having a trocar sleeve fixing protrusion in a lower part thereof and having an injection port fixing protrusion and a fixing groove at a periphery of the lower part, and a coupling member installed at an upper surface of the lower case and having a coupling hole at a periphery of an upper surface of the coupling member; a trocar sleeve installed at the trocar sleeve fixing protrusion of the lower part of the lower case; a lip valve installed within the head unit and having an upper part formed in a circular shape and having a tapered lower part; an insertion unit installed at the upper part of the lip valve; a button unit including an elastic bush fitted to both side surfaces of the lower case of the base unit, button elastically installed at the elastic bush, and press shaft housed within the button and selectively opening the lower part of the lip valve; and a trocar needle introduced into the trocar sleeve through the lip valve or the insertion unit to make a puncture in the abdomen of the patient.

Advantageous Effects

According to the present invention, because a head unit and a base unit are transparently formed, a surgical instrument introduced through a flexible tube can be viewed and thus smoothly introduced.

Further, because a protrusion is formed at an outer circumferential edge of a trocar sleeve, the trocar sleeve is prevented from being separated from the abdomen while performing surgery, and thus a surgical operation can be stably performed.

Further, when a surgical instrument or a gauze is extracted through a lip valve while performing a surgical operation, space is secured by pressing an extension button installed at one side of a head unit and thus the surgical instrument or the gauze can be prevented from being stopped to a lower part of the lip valve.

Further, when performing surgery of internal organs within the abdomen, in order to perform laparoscopic surgery instead of performing open surgery, when introducing a surgical instrument into a trocar sleeve or extracting the surgical instrument from the trocar sleeve, external air is prevented from being injected into the abdomen.

Further, even though any one of surgical instruments necessary for performing laparoscopic surgery is used, a packing closely contacts with an outer circumferential surface of the surgical instrument, thereby maintaining airtightness, and thus external air is prevented from being injected into the abdomen and carbon dioxide is prevented from being discharged.

Further, a trocar sleeve is made of a synthetic resin, ceramic, or a synthetic resin containing silver nano, and a material of the trocar sleeve is not limited thereto and a material that is not harmful to a human body is used in consideration of hygiene of a patient and thus when a surgical operation is performed, secondary infection can be prevented.

DETAILED DESCRIPTION OF EXEMPLARY EMBODIMENTS

Hereinafter, a configuration of a trocar for laparoscopic surgery according to the present invention is described in detail with reference to the attached drawings.

Figure 1:
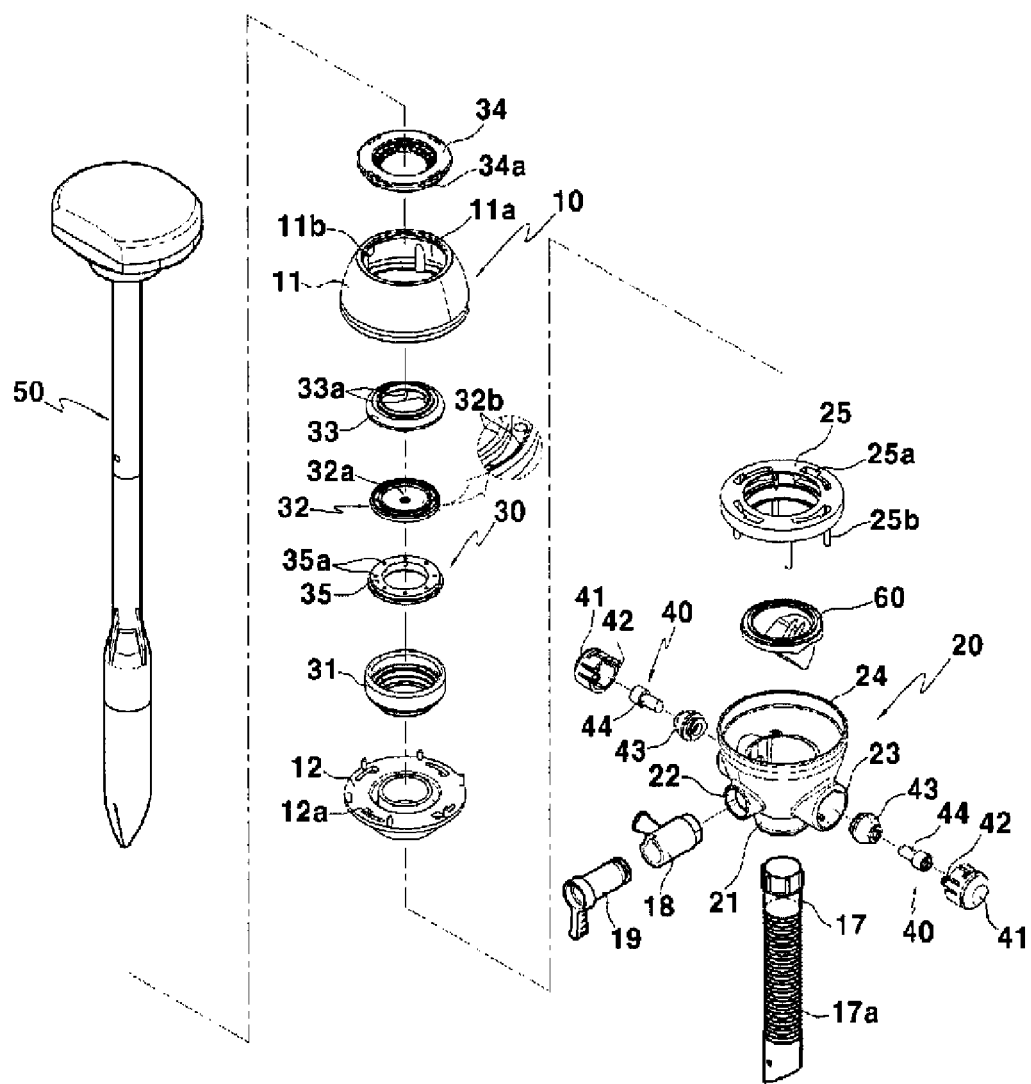
FIG. 1 is an exploded perspective view illustrating a trocar for laparoscopic surgery according to an exemplary embodiment of the present invention.
Figure 2:
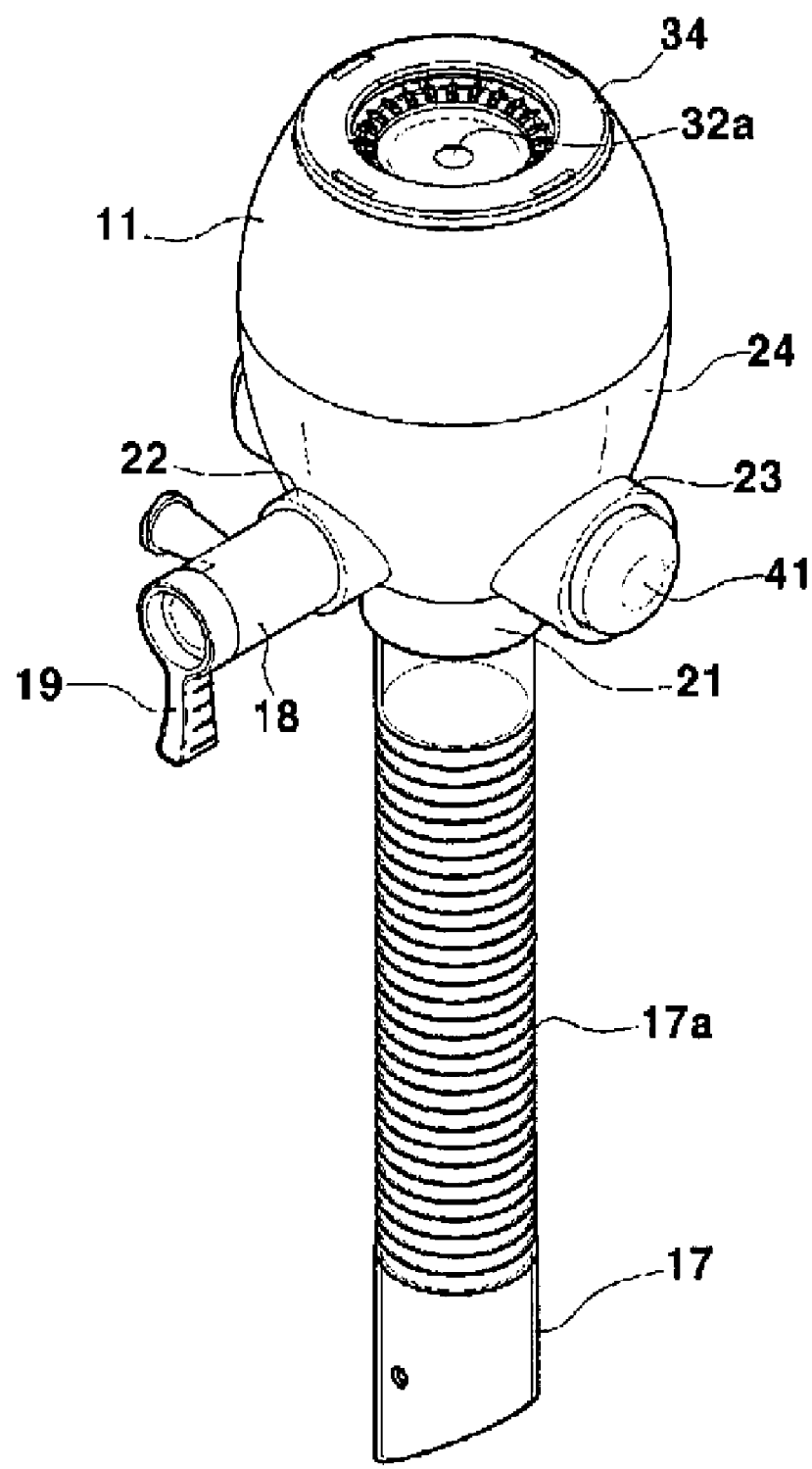
FIG. 2 is a perspective view illustrating a coupling state of the trocar for laparoscopic surgery of FIG. 1.
Figure 3:
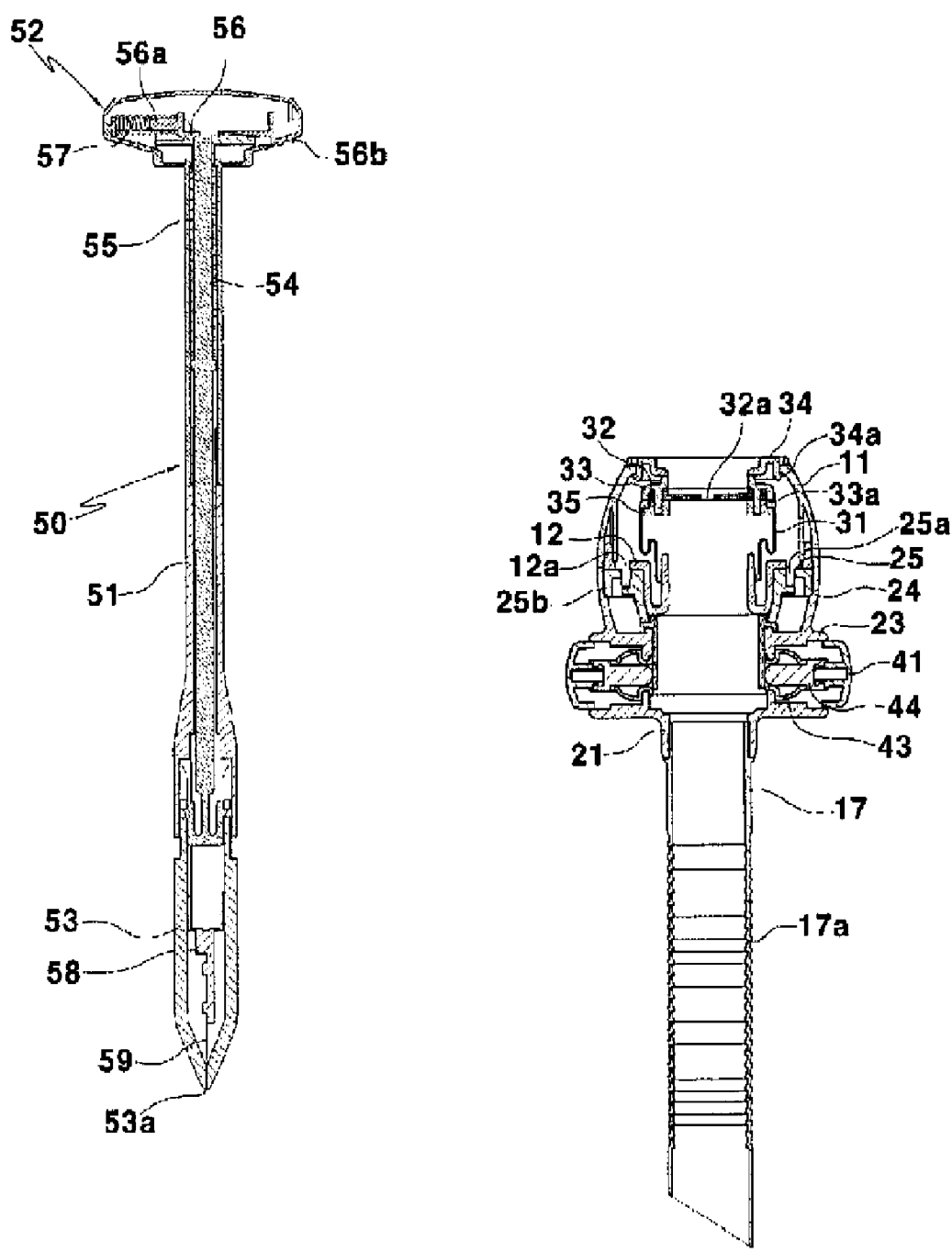
FIG. 3 is a cross-sectional view illustrating a configuration of the trocar for laparoscopic surgery of FIG. 1.
Figure 4:
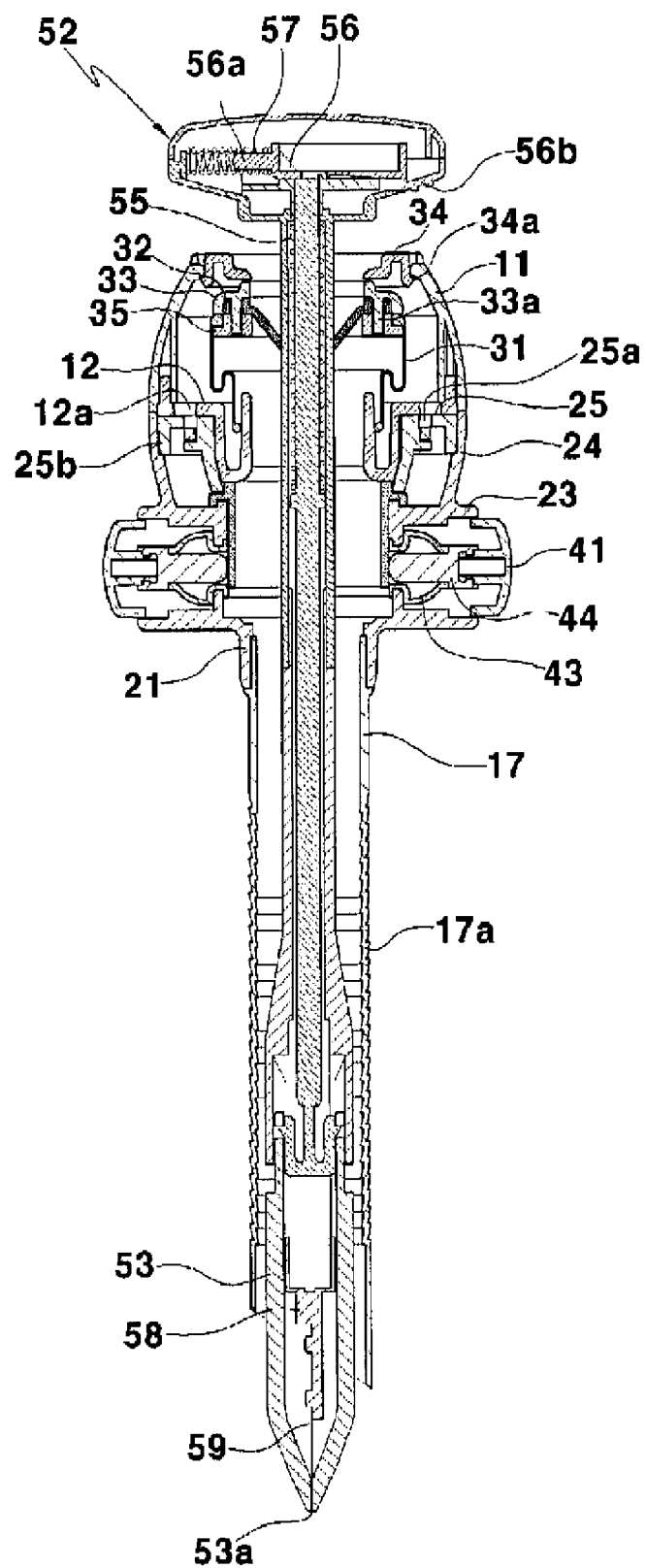
FIG. 4 is a cross-sectional view illustrating a trocar needle installed at the trocar for laparoscopic surgery of FIG. 1.
Figure 5:
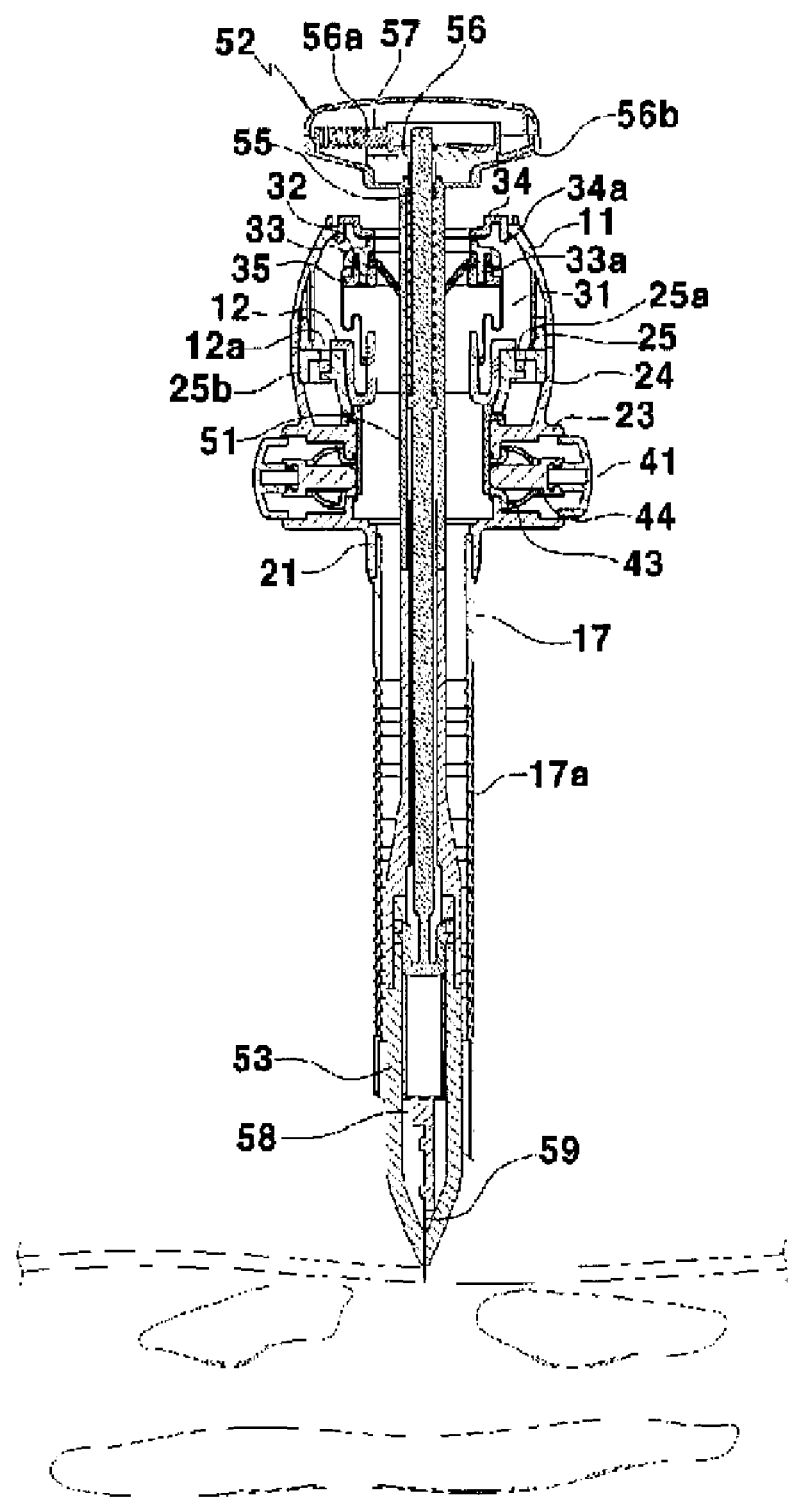
FIGS. 5 and 6 illustrate operation states of the trocar for laparoscopic surgery of FIG. 1.
Figure 6:
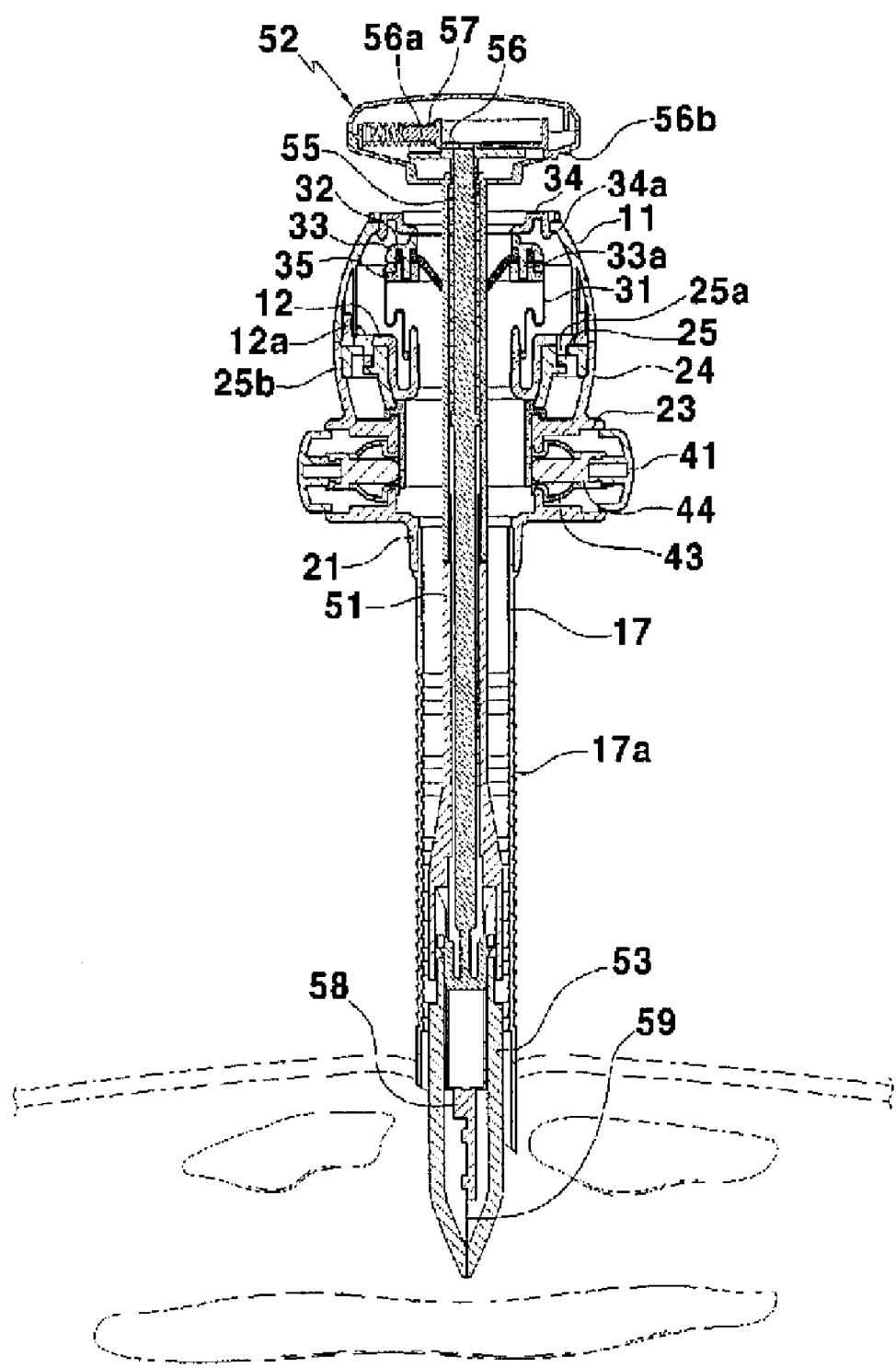
Figure 7:
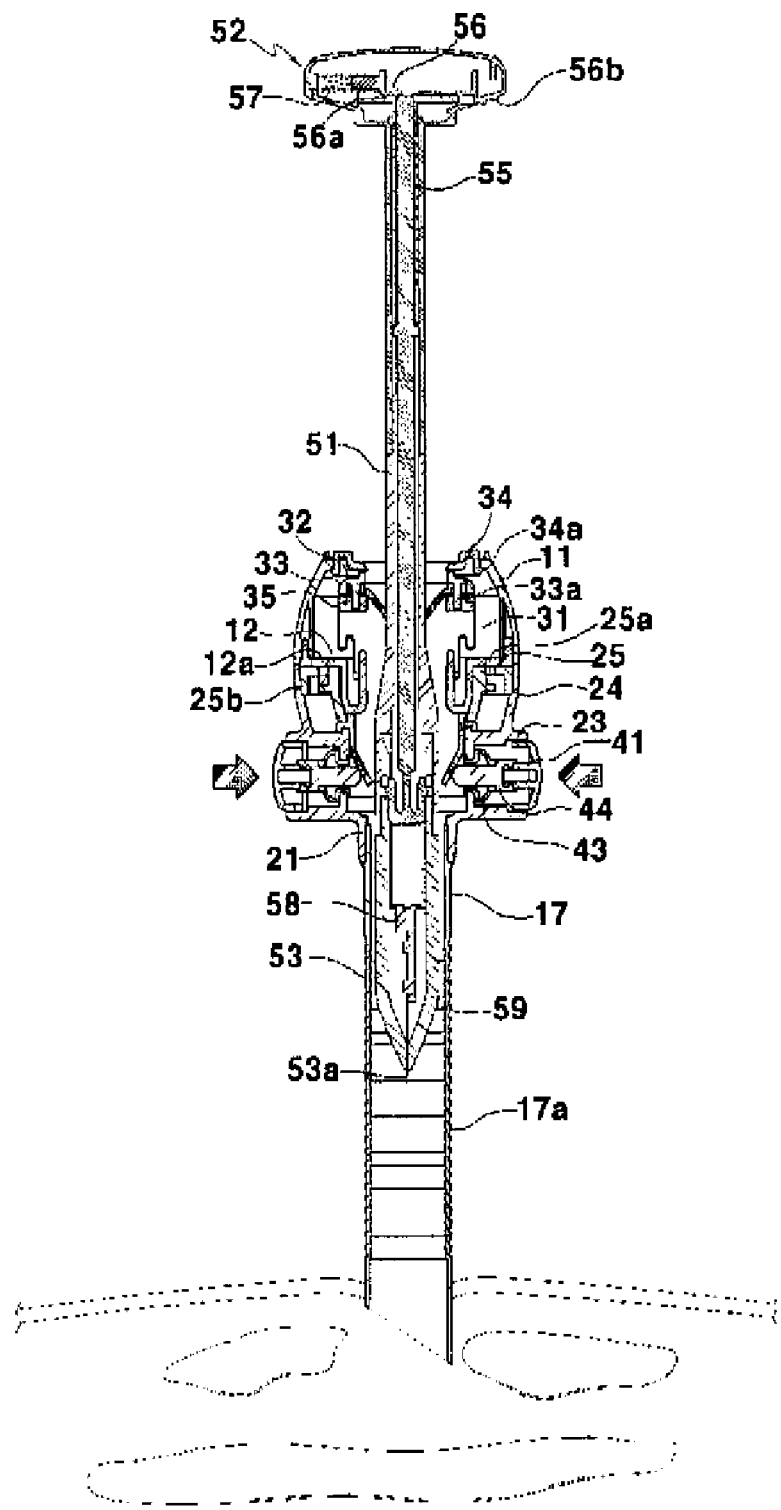
FIG. 7 is a cross-sectional view illustrating another trocar needle installed at a trocar for laparoscopic surgery according to another exemplary embodiment of the present invention.

FIG. 1 is an exploded perspective view illustrating a trocar for laparoscopic surgery according to an exemplary embodiment of the present invention, FIG. 2 is a perspective view illustrating a coupling state of the trocar for laparoscopic surgery of FIG. 1, FIG. 3 is a cross-sectional view illustrating a configuration of the trocar for laparoscopic surgery of FIG. 1, FIG. 4 is a cross-sectional view illustrating a trocar needle installed at the trocar for laparoscopic surgery of FIG. 1, FIGS. 5 and 6 illustrate operation states of the trocar for laparoscopic surgery of FIG. 1, and FIG. 7 is a cross-sectional view illustrating another trocar needle installed at a trocar for laparoscopic surgery according to another exemplary embodiment of the present invention.

Referring to FIGS. 1 to 7, a trocar for laparoscopic surgery according to exemplary embodiments of the present invention includes a head unit 10, a base unit 20, a trocar sleeve 17, a lip valve 60, an insertion unit 30, at least one button unit 40, and a trocar needle 50.

The head unit 10 includes an upper case 11 having a predetermined space at the inside thereof and made of a transparent material, and a lower cover 12 coupled to the bottom of the upper case 11.

An installation hole 11a is formed in an upper part of the upper case 11, and a stopper groove 11b is formed in a portion in which the installation hole 11a is formed.

The lower cover 12 is installed at the bottom of the upper case 11, and a stopper piece 12a is formed at the lower cover 12.

The base unit 20 has a lower case 24 having a predetermined space at the inside thereof and made of a transparent material, a trocar sleeve fixing protrusion 21 is formed to install the trocar sleeve 17 in a lower direction of the lower case 24, and an injection port fixing protrusion 22 is formed at one side of a peripheral surface of the lower case 24.

A coupling member 25 is installed at an upper surface of the lower case 24, coupling holes 25a are formed at the circumference of an upper surface of the coupling member 25, and fixing pins 25b are formed at the bottom of the coupling member 25.

A fixing groove 23 is formed to install the button unit 40 at both sides of a circumferential surface of the lower case 24.

The trocar sleeve 17 is installed at the trocar sleeve fixing protrusion 21 formed at the bottom of the lower case 24.

In order to prevent the trocar sleeve 17 from coming out when performing laparoscopic surgery, a sliding prevention protrusion 17a is formed at the outer circumferential edge of the trocar sleeve 17.

Further, the trocar sleeve 17 is made of one of a synthetic resin, ceramic, and a synthetic resin containing silver nano, a material of the trocar sleeve 17 is not limited thereto, and the trocar sleeve 17 may be made of any material unharmful to a human body and for preventing propagation of bacteria for hygiene of a patient.

A carbon dioxide injection pipe 18 for injecting carbon dioxide into the abdomen is installed at the injection port fixing protrusion 22 formed at one side of the lower case 24 and is used as an inlet for injecting carbon dioxide in order to prevent conglutination of internal organs and a abdominal surface and to secure a surgery space, and a carbon dioxide interception valve 19 is installed at the carbon dioxide injection pipe 18.

An upper part of the lip valve 60 is formed in a circular shape, the lip valve 60 is installed within the base unit 20 and is formed to couple to the trocar needle 50, and both side surfaces of a lower part of the lip valve 60 is tapered toward the center, and thus when the trocar needle 50 is fitted to the lower part of the lip valve 60, the lower part is enlarged, and when the trocar needle 50 is separated from the lower part, the lip valve 60 is intercepted.

The insertion unit 30 is provided within the head unit 10.

The insertion unit 30 includes a flexible pipe 31, an auxiliary ring 35, a packing 32, and a guide ring 33. The flexible pipe 31 is formed to expand and contract, and the lower end of the flexible pipe 31 is fitted to the lower cover 12 and the upper end of the flexible pipe 31 is fitted to a circumferential surface of the auxiliary ring 35.

A fitting hole 35a is formed in the auxiliary ring 35, and the packing 32 made of a silicone material is installed at an upper surface of the fitting hole 35a, an insertion hole 32a for inserting the trocar needle 50 is formed at the center of the packing 32, and elastic fibers 32b of a flexible material are attached to an upper surface and a lower surface of the packing 32 for preventing damage of the packing 32 when a size of the insertion hole 32a is reduced and enlarged.

The guide ring 33 is coupled to an upper surface of the packing 32, and a guide ring fixing pin 33a is formed at a bottom surface of the guide ring 33 and is coupled to the fitting hole 35a of the auxiliary ring 35 and securely fixes the packing 32.

An induction ring 34 is installed at an upper surface of the guide ring 33, and a stopper protrusion 34a is formed at an outer circumferential surface of a lower part of the induction ring 34 and is inserted into and coupled to the stopper groove 11b formed in the upper case 11.

In the button unit 40, a button 41 is coupled to the fixing groove 23, and a fastening pin 42 is formed in the button 41.

A press shaft 44 is provided within the button 41, and an elastic bush 43 for elastically supporting the button 41 is provided within the fixing groove 23.

The trocar needle 50 includes a support pipe 51 of a cylindrical shape, a handle 52 is installed at an upper part of the support pipe 51, and a trocar needle coupling member 53 is coupled to the lower end of the support pipe 51, and a trocar needle entrance hole 53a is formed at the lower and of the trocar needle coupling member 53.

A sliding rod 54 is installed to move in a lower direction at the inside of the support pipe 51, and a first spring 55 is installed in an upper direction of the sliding rod 54.

A slide piece 56 is slidably installed on an a top surface of the sliding rod 54, an elastic protrusion 56a is installed at one side of the slide piece 56, a second spring 57 is installed at the elastic protrusion 56a, and a pressing piece 56b is formed at the other side of the slide piece 56.

A trocar needle fixing member 58 is movably installed at the lower end of the sliding rod 54, and a needle 59 is installed at the trocar needle fixing member 58 and introduced and extracted through the trocar needle entrance hole 53a.

In the present invention having the above-described configuration, in order to make a puncture in the abdomen of a patient, the trocar needle 50 is introduced into the insertion hole 32a and in this case, the insertion hole 32a is enlarged. At this time, since the elastic fibers 32b are attached to both side surfaces of the packing 32, even though the insertion hole 32a is enlarged according to a size of the trocar needle coupling member 53 of the trocar needle 50, the packing 32 is not damaged and maintains a close contact force with an outer side surface of the trocar needle coupling member 53.

When the trocar needle 50 is introduced through the insertion hole 32a, the trocar needle 50 is introduced while opening a lower end portion of the lip valve 60 installed at a lower part of the flexible pipe 31.

As described above, a process of making a puncture in the abdomen by introducing the trocar needle 50 through the lip valve 60 is performed.

while the trocar needle 50 is introduced into the insertion unit 30, the lip valve 60, and the trocar sleeve 17 and closely contacts with the abdomen, the trocar needle coupling member 53 moves toward the support pipe 51, and the needle 59 protrudes to the outside of the trocar needle coupling member 53.

In a state where the needle 59 is not protruded, when the pressing piece 56b installed at one side of the handle 52 is pressed, the slide piece 56 integrally formed with the pressing piece 56b is moved to compress the second spring 57.

At this time, the sliding rod 54 installed within the support pipe 51 is maintained in a state where the sliding rod 54 is able to move toward an opposite direction of the trocar needle fixing member 58, and the needle 59 coupled to the trocar needle fixing member 58 is maintained in a state where the needle 59 does not protrude to the trocar needle entrance hole 53a of the trocar needle coupling member 53.

When a doctor applies a force toward the abdomen of a patient by holding the handle 51 in the state in which the needle 59 is not protruded from the trocar needle coupling member 53, a puncture is formed in the abdomen by the needle 59 while the sliding rod 54 and the trocar needle coupling member 53 are moved in the opposite direction of the trocar needle fixing member 58.

In this case, because the trocar needle coupling member 53 makes a puncture in the abdomen in a state where trocar needle coupling member 52 is pushed to the maximum toward the support pipe 51, after a puncture is formed in an abdominal skin, a pushed state of the trocar needle coupling member 53 is released by an elastic force of the first spring 55 and thus the needle 59 is introduced into the trocar needle coupling member 53, thereby preventing damage of internal organs.

After a puncture is formed in an abdominal skin, the needle 59 is introduced into the trocar needle coupling member 53 and thus in a state in which the trocar needle coupling member 53 has been completely pushed toward the support pipe 51, a stop state of the slide piece 56 installed within the handle 51 is released.

In this case, the trocar needle coupling member 53 continues to make a puncture in a state closely contacting with an abdominal surface, and when a close contact state of the trocar needle coupling member 53 is released, the trocar needle coupling member 53 is in an initial state, i.e. in a state in which the needle 59 is introduced into the trocar needle coupling member 53 by the first spring 55 installed within the support pipe 51, and thus even though the trocar needle 50 continues to be introduced into the abdomen, damage of internal organs is prevented.

In a state in which a puncture is formed in the abdomen using the trocar needle 50, after the trocar needle 50 is extracted, internal organs and an inner surface of the abdomen are separated by injecting carbon dioxide to the abdomen of a patient through the carbon dioxide injection pipe 18 installed at one side of the lower case 25, thereby securing space for easily performing laparoscopic surgery.

In a state in which space is secured between an abdominal surface and internal organs by carbon dioxide, another surgical instrument is introduced into the abdomen, thereby performing laparoscopic surgery.

The surgical instrument is introduced through the insertion hole 32a of the packing 32, and in this case, the insertion hole 32a maintains a close contact state with an outer circumferential surface of the surgical instrument and thus external air is prevented from being injected into the abdomen of the patient and carbon dioxide injected into the abdomen of the patient to secure surgical operation space is prevented from being discharged.

While laparoscopic surgery is performed, as the head unit 10 rotates in directions of several angles by the trocar needle 50, conventionally, the trocar sleeve 17 may be extracted from the abdomen and thus the laparoscopic surgery may be very adversely affected, however in the present invention, because a sliding prevention protrusion 17a is formed at the outer circumferential edge of the trocar sleeve 17, even if the head unit 10 rotates in directions of several angles, the trocar sleeve 17 is prevented from being separated from the abdomen and thus laparoscopic surgery can be safely performed.

Further, because the flexible pipe 31 is provided within the head unit 10, the flexible pipe 31 is expanded and contracted even if a surgical instrument rotates in directions of several angles in a process of performing laparoscopic surgery, and in this case, because the packing 32 maintains a close contact state with an outer circumferential surface of a surgical instrument, the surgical instrument smoothly rotates and thus stable laparoscopic surgery can be performed in a state in which the head unit 10 is fixed.

Further, the button unit 40 installed at one side of the head unit 10 is used when taking out a surgical instrument. Furthermore, the button unit 40 is also used when taking out gauzes used when wiping an affected part or when absorbing other floating matters while performing laparoscopic surgery. In addition, the button unit 40 is also used when taking out extracted materials of the internal organs using a pocket.

When the button unit 40 is manipulated to take out the gauzes or the extracted materials of the internal organs, if a pair of buttons 41 installed at both sides of a circumferential surface of the base unit 20 are simultaneously pressed, the buttons 41 are pushed into the base unit 20 while pressing the elastic bush 43.

While the buttons 41 are pushed, an end portion of the press shaft 44 installed within the button 41 opens a lower part of the lip valve 60 by pressing the lower part of the lip valve 60, and thus the lip valve 60 is opened, whereby the gauzes or the extracted materials of the internal organs can be conveniently taken out.

As described above, in a state in which the lower part of the lip valve 60 is completely opened, when taking out the gauzes or the extracted materials of the internal organs while viewing the transparently formed upper case 11, the gauzes or the extracted materials of the internal organs can be conveniently taken out.

Further, because the upper case 11 is transparently formed, the gauzes or the extracted materials of the internal organs can be taken out without being stopped by other members of the lower part of the lip valve 60.

INDUSTRIAL APPLICABILITY

According to a trocar for laparoscopic surgery according to the present invention, laparoscopic surgery can be performed by forming a small hole instead of performing open surgery in the abdomen of a patient, and thus upon making a puncture in the abdomen, internals organs can be protected, or when laparoscopic surgery is performed by inserting a surgical instrument smaller than a diameter of a trocar sleeve installed at the abdomen, external air and internal carbon dioxide are prevented from being injected or discharged through a packing, or gauzes and extracted materials of internal organs can be easily taken out when performing laparoscopic surgery.

The invention claimed is:

1. A trocar for laparoscopic surgery for performing the laparoscopic surgery through a surgical instrument by making a puncture in the abdomen of a patient, the trocar comprising:
    a head unit comprising an upper case having an installation hole in an upper part thereof and having a stopper groove in an inner circumferential surface of the installation hole, and a lower cover installed at the bottom of the upper case and having a stopper piece at a periphery of an upper surface of the lower cover;
    a base unit comprising a lower case having a trocar sleeve fixing protrusion in a lower part thereof and having an injection port fixing protrusion and a fixing groove at a periphery of the lower part, and a coupling member installed at an upper surface of the lower case and having a coupling hole at a periphery of an upper surface of the coupling member;
    a trocar sleeve installed at the trocar sleeve fixing protrusion of the lower part of the lower case;
    a lip valve installed within the head unit and having an upper part formed in a circular shape and having a tapered lower part;
    an insertion unit installed at the upper part of the lip valve;
    a button unit comprising an elastic bush fitted to both side surfaces of the lower case of the base unit, at least two buttons elastically installed at the elastic bush, and press shaft housed within the at least two buttons, wherein actuation of the at least two buttons moves the press shaft to open the tapered lower part of the lip valve selectively; and
    a trocar needle introduced into the trocar sleeve through the lip valve or the insertion unit to make a puncture in the abdomen of the patient.

2. The trocar of claim 1, wherein the insertion unit comprises:
    a flexible pipe formed to be expanded and contracted;
    an auxiliary ring installed at the upper end of the flexible pipe and having a fitting hole in an upper surface thereof;
    a packing installed at an upper surface of the auxiliary ring and having an insertion hole at the center thereof; and
    a guide ring installed at an upper surface of the auxiliary ring in order to fix the packing and having a guide fixing pin at a bottom surface thereof.

* * * * *